United States Patent [19]
Carey

[11] Patent Number: 5,364,822
[45] Date of Patent: Nov. 15, 1994

[54] PROCESS FOR THE RECOVERY OF GROUP VIII NOBLE METALS

[75] Inventor: John L. Carey, Humberside, England
[73] Assignee: BP Chemicals Limited, London, United Kingdom
[21] Appl. No.: 101,477
[22] Filed: Aug. 2, 1993

[30] Foreign Application Priority Data

Aug. 28, 1992 [GB] United Kingdom ............ 9218346.6

[51] Int. Cl.$^5$ .............. B01J 31/40; B01J 38/68; C22B 11/04; C07C 53/12
[52] U.S. Cl. .............. 502/24; 423/22; 502/25; 502/28; 502/32; 562/891
[58] Field of Search ........ 502/24, 28, 32, 22, 502/25; 423/22; 562/891

[56] References Cited

U.S. PATENT DOCUMENTS

| | | | |
|---|---|---|---|
| 3,420,873 | 1/1969 | Olivier | 260/492 |
| 3,547,964 | 12/1970 | Olivier | 260/429 |
| 3,641,076 | 2/1972 | Booth | 260/429 |
| 3,857,895 | 12/1974 | Booth | 264/604 |
| 4,275,252 | 6/1981 | Imai et al. | 568/909 |
| 4,297,239 | 10/1981 | Mueller et al. | 502/24 |
| 4,329,521 | 5/1982 | Homeier et al. | 502/26 |
| 4,333,884 | 6/1982 | Kubbeler | 260/546 |
| 4,340,569 | 7/1982 | Davidson et al. | 423/22 |
| 4,340,570 | 7/1982 | Davison | 423/22 |
| 4,341,741 | 7/1982 | Davison et al. | 423/22 |
| 4,364,907 | 12/1982 | Barnes | 423/22 |
| 4,374,070 | 2/1983 | Larktham et al. | 260/549 |
| 4,374,278 | 2/1983 | Bryant et al. | 568/454 |
| 4,374,287 | 2/1983 | Imai | 568/909 |
| 4,388,217 | 7/1983 | Hembre | 423/22 |
| 4,430,273 | 2/1984 | Erpenbach et al. | 260/546 |
| 4,434,241 | 2/1984 | Larkins, Jr. | 502/24 |
| 4,476,237 | 10/1984 | Porcelli | 502/31 |
| 4,476,238 | 10/1984 | Palmer et al. | 502/31 |
| 4,504,588 | 3/1985 | Gariner et al. | 502/24 |
| 4,578,368 | 3/1986 | Zoeller | 502/28 |
| 4,746,640 | 5/1988 | Erpenbach et al. | 502/24 |
| 4,944,927 | 7/1990 | Culliver | 423/22 |
| 4,945,075 | 7/1990 | Cushman et al. | 502/24 |
| 5,002,914 | 3/1991 | Erpenbach et al. | 502/24 |
| 5,003,104 | 3/1991 | Pavcik et al. | 562/517 |
| 5,085,835 | 2/1992 | Weber et al. | 423/22 |
| 5,100,850 | 3/1992 | Fillers et al. | 502/24 |
| 5,214,205 | 5/1993 | Castanes et al. | 562/891 |
| 5,260,490 | 11/1993 | Forster et al. | 568/454 |
| 5,298,586 | 3/1994 | Beevok et al. | 562/891 |

FOREIGN PATENT DOCUMENTS

| | | |
|---|---|---|
| 879601 | 8/1971 | Canada. |
| 0255389 | 2/1983 | European Pat. Off.. |
| 0087870 | 9/1983 | European Pat. Off.. |
| 0255389 | 2/1988 | European Pat. Off.. |
| 0314352 | 5/1989 | European Pat. Off. ...... 502/24 |
| 0314352 | 5/1989 | European Pat. Off.. |
| 337262 | 10/1989 | European Pat. Off.. |
| 350922 | 1/1990 | European Pat. Off.. |
| 380911 | 8/1990 | European Pat. Off.. |
| 0479463 | 4/1992 | European Pat. Off.. |
| 1290535 | of 0000 | Germany. |
| 6033040 | 4/1981 | Japan. |
| 87005013 | 2/1987 | Japan. |
| 62-072645 | 4/1987 | Japan. |
| 1233121 | 5/1971 | United Kingdom. |
| 1253758 | 11/1971 | United Kingdom. |
| 1424818 | 2/1975 | United Kingdom. |
| 1468940 | 3/1977 | United Kingdom. |
| 1538783 | 1/1979 | United Kingdom. |
| 2094284 | 9/1982 | United Kingdom. |
| 2094285 | 9/1982 | United Kingdom. |
| 2095221 | 9/1982 | United Kingdom. |
| 8201829 | 6/1982 | WIPO. |
| 8606750 | 11/1986 | WIPO. |

OTHER PUBLICATIONS

Patent Abstracts of Japan, vol. 11, No. 268, Aug. 29, 1987.

Primary Examiner—Paul E. Konopka
Attorney, Agent, or Firm—Brooks Haidt Haffner & Delahunty

[57] ABSTRACT

In the process for recovery of Group VIII noble metal carbonylation catalyst from a process stream which also contains tar produced during a carbonylation process for carboxylic acid anhydride production, the process stream is diluted with alkyl halide and then extracted with a water, carboxylic acid, iodide salt alkyl halide solution, the iodide salt being a co-promoter derived from the carbonylation process. The recovered noble metal may be recycled to the carbonylation process with iodide salt co-promoter.

11 Claims, 2 Drawing Sheets

PROCESS FOR THE RECOVERY OF GROUP VIII NOBLE METALS

The present invention relates to the recovery of Group VIII noble metal catalysts from the products arising from carbonylation processes. More specifically, the present invention relates to a process for recovery of Group VIII noble metal catalysts from process streams containing high boiling organic polymers (known in the art as tars) which have been produced as by-products in carbonylation processes.

Group VIII noble metal-catalysed carbonylation processes are now well known in the art and are in some cases operated commercially. Typical examples of such processes include (a) the rhodium catalysed hydroformylation of olefins to higher alcohols, aldehydes and ketones; (b) the rhodium catalysed carbonylation of methanol to acetic acid; (c) the rhodium catalysed carbonylation of methyl acetate to acetic anhydride or ethylidene diacetate and (d) the rhodium catalysed carbonylation of methyl acetate, water and methanol to produce both acetic anhydride and acetic acid as described in EP 87870.

A problem often encountered with carbonylation processes of this type is that, in addition to the desired products, there is often formed, as by-product, considerable quantities of a high boiling organic polymer (tar). On commercial plants the formation of such tars is particularly undesirable since they tend to build up in the carbonylation reactor and eventually reduce the efficiency of the process. To avoid build up of such tars, it is therefore necessary to remove continually or intermittently a side process stream from, for example, a catalyst recycle stream or the carbonylation reactor liquid contents and which stream contains tar as well as Group VIII noble metal carbonylation catalyst and associated promoters and co-promoters. This side process stream is treated in a way such that the Group VIII noble metal catalyst and associated promoters and co-promoters are recovered therefrom and can be returned directly or indirectly to the carbonylation reactor whilst the tars can be disposed of.

One approach to such a recovery process is to distil the process stream to form a solid residue comprising mainly Group VIII noble metal, promoters and co-promoters and then treat the residue with a solubilising liquid, such as a strong acid. The Group VIII noble metal, promoters and copromoters dissolve in the solubilising liquid and can then be recovered from the solubilising liquid using standard techniques. Although such a process can in principle be used on a commercial plant it suffers from the disadvantage that it cannot easily be operated continuously.

Processes, which can be operated continuously, have been described for example in U.S. Pat. No. 4,476,237, U.S. Pat. No. 4,388,217, U.S. Pat. No. 4,364,907, GB-A-2094284 and EP-A-0255389.

U.S. Pat. No. 4,476,237 describes an extraction process for removing tars.

U.S. Pat. No. 4,388,217 describes a process for the recovery of catalyst values from a catalyst-tar solution derived from a production system in which acetic anhydride is prepared by carbonylating methyl acetate in the presence of rhodium, lithium and methyl iodide wherein the catalyst-tar solution is submitted to an extraction using methyl iodide and aqueous hydrogen iodide and catalyst values are recovered in the aqueous phase.

U.S. Pat. No. 4,364,907 describes a process for the recovery of rhodium from tar in which a rhodium-containing catalyst-tar solution is extracted in a first extraction using methyl iodide and aqueous hydrogen iodide, thereby recovering catalyst values in the aqueous phase and tar containing residual rhodium in the methyl iodide phase. The residual rhodium-containing tar is submitted to a second extraction using water-immiscible, inert solvent for the tar and aqueous ammonia to obtain residual rhodium in the aqueous phase.

GB-A-2094284 describes a process for recovering Group VIII noble metals bound to residues of noble metal catalysed carbonylation reactions wherein said residues are separated from the carbonylation reaction mixture and are treated with a reagent comprising an amine, thereby freeing said noble metals from said residues and enabling said bound noble metals to be extracted by subsequent contact with a halogen acid. GB-A-2094285 and GB-A-2095221 describe similar processes. According to these three patent applications the halogen acid may be used as an aqueous solution and a solvent may be present to dissolve the residue and separate it from the aqueous layer which forms and which contains the extracted noble metal. One disadvantage with the use of extractant solutions containing hydrogen iodide is that aqueous hydrogen iodide is very corrosive, so that special equipment is required. Another disadvantage is that recycle of the aqueous phase directly to the carbonylation reactor leads to a build up of methyl iodide in the system because of the presence of the hydrogen iodide in the stream. Consequently, it may be necessary to employ ancillary equipment to recover the excess methyl iodide and convert it back to hydrogen iodide or to purge excess iodide from the system. Alternatively, it may be necessary to recover the rhodium from the aqueous stream and separately recycle it to the carbonylation reactor.

U.S. patent number U.S. Pat. No. 4,944,927 describes a continuous process for recovering a Group VIII noble metal catalyst from tar generated by the polymerisation of ketene or the reaction of ketene with one or more of methyl acetate, acetic anhydride or ethylidene diacetate, which process comprises the steps of diluting the tar containing the Group VIII noble metal catalyst with methyl iodide to produce a process stream which is thereafter contacted with an extracting stream comprising acetic acid in water so that the Group VIII metal is extracted into the extracting stream.

None of these processes is entirely satisfactory. Therefore, there remains a need for an improved process for the recovery of Group VIII noble metal catalysts from tar-containing process streams.

Thus, according to the present invention there is provided a process for the recovery of Group VIII noble metal catalyst from a process stream comprising Group VIII noble metal carbonylation catalyst and tar, which tar has been generated during a carbonylation process for the production of carboxylic acid anhydride in the presence of a Group VIII noble metal carbonylation catalyst, a halide promoter and an iodide salt co-promoter, which recovery process comprises the steps of:

(a) mixing the process stream with alkyl halide to produce a composition comprising alkyl halide, tar and Group VIII noble metal catalyst;

(b) contacting the composition from step (a) with an extracting solution comprising (i) water, (ii) carboxylic acid corresponding to the carboxylic anhydride product of the carbonylation process, (iii) iodide salt co-promoter derived from the carbonylation process and (iv) alkyl halide, to produce an aqueous phase comprising Group VIII noble metal catalyst and an alkyl halide phase comprising tar; and (c) separating the aqueous and alkyl halide phases.

The present invention solves the need described above by the use in the aqueous extracting solution of an iodide salt co-promoter which has been derived from the carbonylation process.

The iodide salt in the extracting solution facilitates extraction of the noble metal catalyst into the aqueous phase. Also, since it is derived from the carbonylation process it may be recycled to the carbonylation process with the noble metal catalyst.

The process of the present invention may be used to recover Group VIII noble metal carbonylation catalysts from process streams containing tars produced in a carbonylation process for the production of carboxylic acid anhydrides preferably acetic anhydride optionally with coproduction of acetic acid for example as described in U.S. Pat. No. 4,374,070, U.S. Pat. No. 5,003,104 and EP-A-87870.

The term Group VIII noble metal means any one or more of the metals ruthenium, osmium, rhodium, iridium, palladium and platinum. Preferably, the Group VIII noble metal is either rhodium or iridium, more preferably rhodium.

The carbonylation process which generates the tar involves reaction of an alkyl ester, for example methyl acetate, or a dialkyl ether for example dimethyl ether or of reactive derivatives thereof with carbon monoxide in the presence of a Group VIII noble metal carbonylation catalyst and a halide promoter and an iodide salt co-promoter. The use of such promoters and co-promoters has been discussed at length in other patents such as GB 1468940, GB 1538783, GB 1233121, GB 1253758, EP-A-0479463, U.S. Pat. No. 4,430,273 and U.S. Pat. No. 4,374,070 and hence are familiar to the skilled man. In the case of rhodium catalysts a halide promoter such as a bromide or iodide compound preferably methyl iodide may be used as promoter along with one or more iodide salt co-promoters such as iodide salts of quaternary amines, phosphines, arsines, stibines and metals such as chromium, zirconium, vanadium, lithium and the like. Both simple and multiple catalyst/promoter/copromoter systems based on these components can be recovered using the process of the present invention.

The tar is a high molecular weight organic polymer which is produced as a by-product in Group VIII noble metal-catalysed carbonylations. Most preferably, the tar is the by-product of a carbonylation process for the production of a carboxylic acid anhydride such as acetic anhydride. Without wishing to be bound by any theory it is believed that in carbonylation processes for the production of acetic anhydride, the tar may be generated by polymerisation of ketene and/or reaction of ketene with methyl acetate, acetic anhydride, ethylidene diacetate and the like and/or by condensation of acetone by-product. The character of such tars has been discussed in U.S. Pat. No. 4,388,217.

The process stream containing tar and Group VIII noble metal catalyst may be derived from the carbonylation process intermitently or continuously by removing a liquid side stream or recycle stream from the carbonylation reactor. Preferably the process stream is concentrated to remove volatile material which has the advantage of assisting subsequent phase separation. Most preferably the process stream is a side stream of the liquid phase recycle from a carbonylation product recovery flash stage.

Thus, in this embodiment, liquid carbonylation composition comprising a Group VIII noble metal carbonylation catalyst, a halide promoter, an iodide salt co-promoter, carboxylic acid anhydride and/or its corresponding carboxylic acid, carbonylation reactant such as alkyl ester or dialkyl ether and tar is withdrawn from the carbonylation reactor and subjected to a flash separation with or without the addition of heat to produce (a) a vapour fraction comprising carbonylation product and volatile reactant and promoters and (b) a liquid fraction comprising involatile Group VIII noble metal carbonylation catalyst, iodide salt co-promoter, carboxylic acid anhydride and/or its corresponding acid, and tar. At least a part of the liquid fraction is treated according to the process of the present invention, the remainder being recycled to the carbonylation reactor.

Preferably, the process stream containing tar and Group VIII noble metal is contacted with water to convert carboxylic acid anhydrides to corresponding carboxylic acids since, if such anhydrides contact water in the process of the invention, local hot spots can result. This contacting with water may be performed prior to the process of the present invention or as part of the process of the present invention.

In steps (a) and (b) the alkyl halide preferably corresponds to the alkyl halide promoter used in the carbonylation process, preferably an iodide or bromide, most preferably an iodide. For acetic anhydride production the alkyl halide is preferably methyl iodide. For a carbonylation process using rhodium/methyl iodide/NN' dimethyl imidazolium iodide as catalyst/promoter/co-promoter for the production of acetic anhydride, the ratio of tar-containing process stream to methyl iodide stream in step (a) may typically be in the range 1:0.3 to 1:3 by weight.

In step (b) of the process of the present invention the iodide salt co-promoters in the extracting solution are preferably iodide salts of quaternary amine, phosphine, arsenic or antimony compounds or of metals such as lithium, preferably iodide salts of quaternary amine or phosphine compounds and lithium. More than one iodide salt may be used. The use of such compounds as carbonylation catalyst co-promoters but not as catalyst stabilisers in a catalyst recovery process has previously been described for example in U.S. Pat. No. 4,333,884, EP-A-0479463 and U.S. Pat. No. 4,374,070. Thus, suitable quaternary phosphine stabilisers comprise iodide salts of quaternary organophosphorus compounds such as tributyl-methyl phosphonium iodide, trioctyl-methyl phosphonium iodide, trilauyl-methyl phosphonium iodide, triphenyl-methyl phosphonium iodide and the like, which compounds are described in U.S. Pat. No. 4,333,884. The use of lithium iodide as a carbonylation co-promoter is described in U.S. Pat. No. 4,374,070.

Preferably, the iodide salt co-promoter in the extracting solution is an iodide salt of a quaternary amine compound such as a heterocyclic aromatic compound in which at least one of the hereto atoms is a quaternary nitrogen atom. For example N-methylpyridinium iodide; N,N'-dimethylimidazolium iodide; N-methyl-3-picolinium iodide; N-methyl-2,4-lutidinium iodide; N- methyl-3,4-lutidinium iodide; N-methyl-quinolinium iodide; which compounds have been described in U.S. Pat. No. 4,333,884 and U.S. Pat. No. 4,430,273, or alkylated derivatives thereof, although less substituted derivatives are preferred over more substituted derivatives. Most preferably, the iodide salt co-promoter in the extracting solution is an iodide salt of a quaternary amine compound such as described in European published patent application EP-A-0479463 that is:

1,3-dialkyl-4-methylimidazolium iodide;
1,3-dialkyl-4-ethylimidazolium iodide;
1,3-dialkyl-4-n-propylimidazolium iodide;
1,3-dialkyl-4-isopropylimidazolium iodide;
1,3-dialkyl-4-n-butylimidazolium iodide;
1,3-dialkyl-4-sec-butylimidazolium iodide;
1,3-dialkyl-4-tert-butylimidazolium iodide;
1,3-dialkyl-2,4,5-trimethylimidazolium iodide and mixtures thereof where the alkyl groups are independently $C_1$–$C_{20}$ alkyl.

That the iodide salt co-promoter in the extracting solution is derived from the carbonylation process which generates the tar has the advantage that iodide salt returned to the carbonylation process with recovered Group VIII noble metal catalyst is compatable with the carbonylation process. Most preferably, the iodide salt co-promoter is derived from the carbonylation process in a pre-extraction step. Thus, in step (a) the process stream which also comprises suitable iodide salt co-promoter as well as Group VIII noble metal carbonylation catalyst, carboxylic acid anhydride and/or its corresponding acid, and tar is mixed with alkyl halide and water to produce (i) a pre-extraction aqueous phase comprising water, carboxylic acid corresponding to the carboxylic acid anhydride product of the carbonylation process, alkyl halide and iodide salt co-promoter and (ii) a pre-extraction alkyl halide phase comprising alkyl halide, tar and Group VIII noble metal catalyst. The pre-extraction phases are then separated and the water, carboxylic acid and/or alkyl halide concentrations in the pre-extraction aqueous phase may be adjusted to required values suitable for use as all or part of the extracting solution for step (b) of the process of the present invention; the pre-extraction alkyl halide phase and adjusted pre-extraction aqueous phase are then contacted in step (b) of the process of the present invention. This has the advantage that there is compatability with the carbonylation process of iodide salt co-promoter returned with the Group VIII noble metal and also build up of iodide salt co-promoter in the process can be avoided.

In the pre-extraction the ratios of water to alkyl halide to process stream depend upon such factors as other components present in the process stream. The less water used the higher the concentration of iodide salt co-promoter in the pre-extraction aqueous phase. Preferably, the amount of water used should be as low as possible consistant with achieving phase separation. For a carbonylation process using rhodium/methyl iodide/NN' dimethyl imidazolium iodide as catalyst/promoter/co-promoter for the production of acetic anhydride the ratio of water to process stream derived from a carbonylation product recovery flash stage is typically in the range 0.1:1 to 2:1. Typically the pre-extraction aqueous phase may comprise 60–90% of the iodide salt co-promoter from the process stream used. The pre-extraction aqueous phase will contain some Group VIII noble metal catalyst and tar due to the presence of carboxylic acid from the carbonylation process and/or hydrolysis of carbonylation acid anhydride product. This pre-extraction step may be used to hydrolyse carboxylic acid anhydride in the tar-containing process stream and thereby prevent hot spots in the subsequent steps of the process.

In the pre-extraction the water, iodide salt-containing process stream and alkyl halide may be mixed together in any sequence. Preferably, the process stream and alkyl halide are pre-mixed before the water is added.

The pre-extraction step may be performed at any suitable temperature provided that phase separation can be achieved. Thus the water and process stream may be mixed at any suitable temperature preferably elevated to facilitate hydrolysis of anhydride, for example at about 100° C. and then cooled to facilitate phase separation, preferably at 5° C. to 25° C. The pre-extraction step may be performed at any suitable pressure, preferably 0 to 5 barg. Static or moving mixers may be used to mix the water, alkyl halide and iodide salt co-promoter containing process stream in the pre-extraction step.

In step (b) of the process of the present invention the extracting solution is preferably pre-saturated with alkyl halide prior to contacting with the alkyl halide-containing composition from step (a). This may be achieved at least in part by the pre-extraction step of mixing the process stream comprising tar, Group VIII noble metal and iodide salt co-promoter with water and alkyl halide to provide a pre-extraction aqueous phase for use as at least part of the extracting solution.

Whether or not prepared by pre-extraction, for a carbonylation process producing acetic anhydride the ratio of acetic acid: water in the extracting solution is preferably in the range 1:1 to 10:1 but depends upon the concentration of other components. The ratio is preferably high subject to maintaining phase separation. The extracting solution preferably comprises between 30 and 70% by weight acetic acid. The ratio of carboxylic acid to water in the extracting solution prepared by pre-extraction is adjusted by addition of water, carboxylic acid and/or alkyl halide prior to use in step (b).

The concentration of iodide salt co-promoter in the extracting solution in step (b) may be any value up to its limit of solubility. For quaternery amine iodide salts the concentration is typically in the range of 1 to 30% by weight. It has been found in acetic anhydride derived tar extraction that increasing catalyst stabiliser concentration, for example achieved by using less water in the pre-extraction step, reduces the amount of acetic acid with respect to water required to achieve a given Group VIII noble metal extraction in the process of the present invention. Excess water in the extracting solution is not preferred as this is recycled to the carbonylation process with the recovered catalyst and can reduce the amount of carboxylic anhydride produced.

In step (b) of the process of the present invention the tar-containing composition from step (a) with or without pre-extraction and the extracting solution are preferably contacted in counter-current manner, preferably with stirring or agitation to achieve good contact without axial mixing. Typically, this is effected by introducing the denser composition from step (a) into the top of a multistage extraction column such as a Kuhni column and introducing the lighter extracting solution into the base of the column; the aqueous and alkyl halide phases being removed from the top and bottom respectively of the column. Preferably, this extraction process is performed at temperatures less than 25° C. provided that the liquids do not freeze and that phase separation is maintained. Any suitable pressure may be used for example 0 to 5 barg provided that phase separation is maintained.

After separation in step (c) of the process of the present invention the aqueous phase comprises the Group VIII noble metal and iodide salt co-promoters and may be recycled to the carbonylation process. The alkyl halide phase comprising tar is passed to a separation unit, for example an evaporator where the tar and alkyl halide are separated. The tar is disposed of and the alkyl halide is recycled for use in the process of the present invention and/or the carbonylation process.

BRIEF DESCRIPTION OF THE DRAWINGS

The invention will now be illustrated by reference to the following examples and drawings in which.

Figure 1:
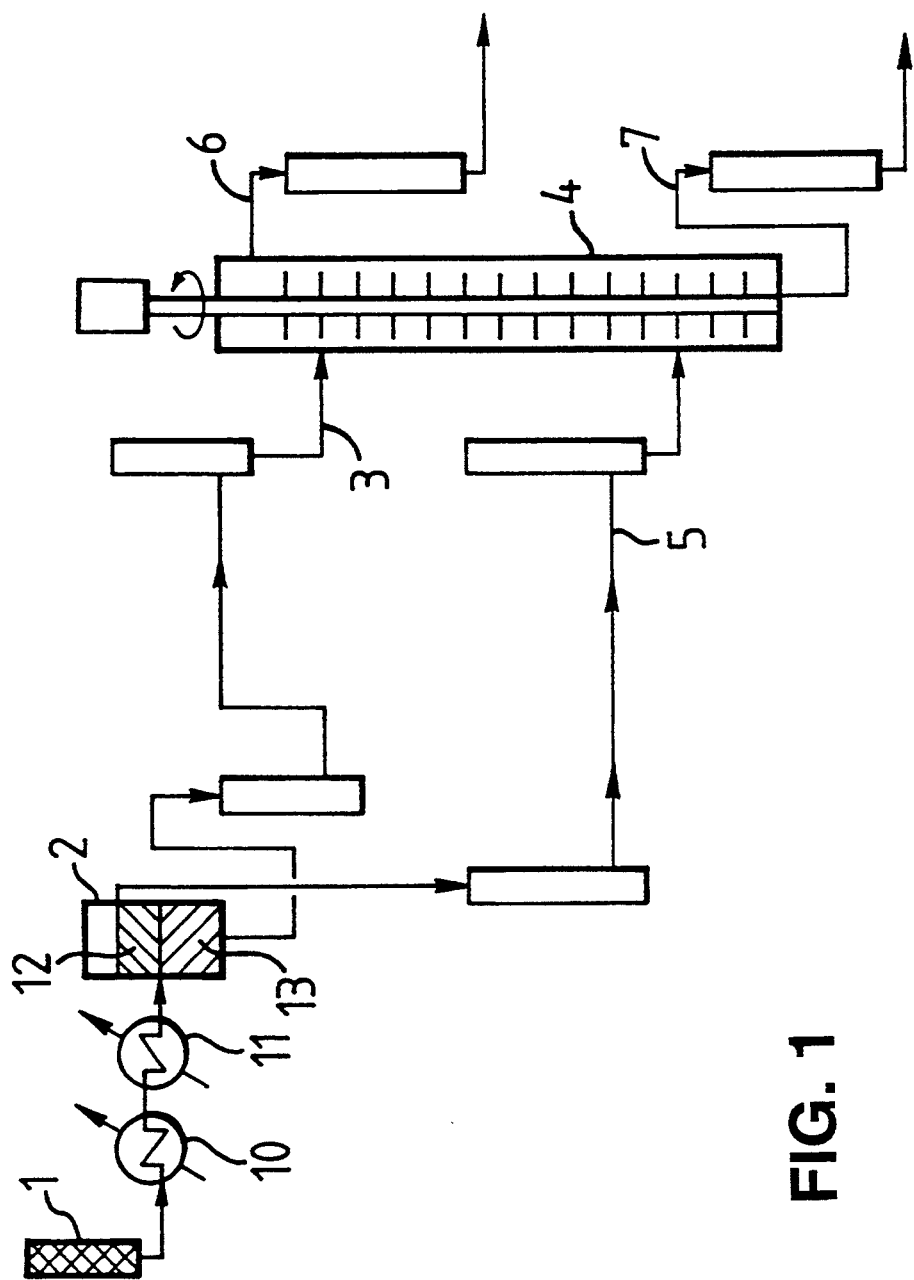
FIG. 1 represents in schematic form an apparatus for use in the process of the present invention and FIG. 2 is a graph of experimental results obtained demonstrating the process of the present invention.

The process of the present invention may be carried out for example using the apparatus shown in FIG. 1. In this case a catalyst recycle stream (CRS) being a side stream of liquid phase from a carbonylation product recovery flash stage from a rhodium-catalysed carbonylation process for the co-production of acetic acid and acetic anhydride and comprising rhodium catalyst, methyl iodide carbonylation promoter, iodide salt of a quaternary amine carbonylation co-promoter (such as N,N'-dimethyl imidazolium iodide and its alkylated derivatives), tar and carbonylation reaction products is withdrawn from the carbonylation process, diluted with methyl iodide (MeI) and fed into static mixers (1). Water is also fed into the mixers. In the mixers the water, CRS and MeI are mixed and pass through cooler (10) and chiller (11) into setting vessel (2) where they are separated to produce a pre-extraction aqueous phase (12) and a pre-extraction methyl iodide phase (13). Prior to the coolers, in the pre-extraction mixers acetic anhydride is hydrolysed to acetic acid. The pre-extraction aqueous phase is saturated with methyl iodide. The pre-extraction methyl iodide phase comprising tar and Group VIII noble metal catalyst is fed alone line (3) to the top of a multistage extraction Kuhni column (4). The pre-extraction aqueous phase comprising acetic acid, water, methyl iodide and iodide salt of quaternary amine co-promoter has its methyl iodide and acetic acid concentrations adjusted to ensure that it is saturated with methyl iodide by addition of methyl iodide and acetic acid in line (5) and is then fed as extracting solution to the bottom of the Kuhni column (4). In the Kuhni column the methyl iodide-containing composition from the pre-extraction and aqueous extracting solution are contacted to produce an aqueous phase comprising Group VIII noble metal and iodide salt of quaternary amine co-promoter and a methyl iodide phase comprising tar. The aqueous phase is removed from the top of the Kuhni column through line (6) and recycled to the carbonylation process (not shown). The tar-containing methyl iodide phase is removed from the base of the Kuhni column through line (7). The methyl iodide is separated from the tar in the methyl iodide phase, for example in an evaporator (not shown); the tar being disposed of e.g. by burning and the methyl iodide being recycled to mix with incoming tar-containing process stream in the process of the present invention and/or to the carbonylation process.

The improved efficiency of extraction which is obtained using the process of the present invention will now be further illustrated by the following Examples. The apparatus used was similar to that shown in FIG. 1 except that a stirred mixer was used to mix water, methyl iodide and CRS which had already had its acetic anhydride hydrolysed by the addition of some water. Also the two parts of the process, pre-extraction and the Kuhni column were operated separately.

In the Examples the following definitions of extraction efficiencies apply:

rhodium efficiency (%)=mass flow rate of rhodium in aqueous phase×100 mass flow rate of rhodium in aqueous and alkyl halide phases tar efficiency (%)=mass flow rate of tar in alkyl halide×100 mass flow rate of tar in alkyl halide and aqueous phases quaternary amine salt (QAS) efficiency (%)=mass flow rate of quaternary amine salt in aqueous phase×100 mass flow rate of QAS in aqueous and alkyl halide phases.

A process stream (CRS) from the liquid phase of a product recovery flash stage of a carbonylation process for the production of acetic acid and acetic anhydride from methanol and methyl acetate in the presence of a rhodium/methyl iodide/N,N'-dimethylimidazolium iodide (quaternary amine salt, QAS) catalyst system was used in the following Experiments. The stream had the following typical composition (by weight):

| | |
|---|---|
| Acetic anhydride | 16.5% |
| Acetic acid | 30.5% |
| Methyl iodide (MeI) | 3.5% |
| Methyl acetate | 8.9% |
| Tar | 19.6% |
| Quaternary amine salt (QAS) co-promoter | 21.0% |
| Rhodium catalyst | 700 ppm rhodium |

The process stream was mixed with crude methyl iodide (99.4% methyl iodide 0.6% methyl acetate) and deionised water in the weight ratio CRS: crude methyl iodide: water of 47.5:47.5:5 and allowed to stand for 2 hours to hydrolyse the acetic anhydride and provide a methyl iodide-diluted, tar-containing process stream for use in subsequent processing steps.

The pre-extraction stage was demonstrated by continuously feeding the methyl iodide-diluted tar stream together with further water into a stirred mixing vessel having a residence time of greater than 60 minutes and a temperature of less than 30° C. with good mixing. The contents of the mixer vessel passed to a settler vessel from which was taken a pre-extraction methyl iodide phase comprising tar and rhodium catalyst and a pre-extraction aqueous phase comprising quaternary amine iodide salt, acetic acid and methyl iodide.

Analysis of the two pre-extraction phases showed that some rhodium and quaternary amine salt passed into the pre-extraction aqueous phase and some tar passed into the pre-extraction aqueous phase. Experiments were performed using differing amounts of water and differing CRS/methyl iodide ratios and the rhodium, tar and stabiliser extraction efficiencies were calculated as defined above. The results are shown in Table 1. The results in Table 1

TABLE 1

SUMMARY OF RESULTS FROM PRE-EXTRACTION STAGE

| Expt. No. | FEED FLOW RATIOS | | EXTRACTION EFFICIENCIES | | |
|---|---|---|---|---|---|
| | Water CRS | MeI CRS | Rh Eff. % | Tar Eff. % | QAS Eff. % |
| 29 | 0.338 | 0.728 | 19.2 | 76.8 | 86.6 |
| 23 | 0.340 | 0.728 | | 71.8 | 81.9 |
| 30 | 0.342 | 0.728 | 21 | 79.7 | 85.2 |
| 6 | 0.264 | 1 | | 76.3 | 85.8 |
| 3 | 0.272 | 1 | 19.3 | 76.5 | 87.7 |
| 14 | 0.280 | 1 | 35.5 | 72.4 | 87.2 |
| 9 | 0.282 | 1 | 25.5 | 75.8 | 85.7 |
| 7 | 0.318 | 1 | 27.7 | 74.3 | 88.1 |
| 4 | 0.332 | 1 | | | 85.7 |
| Y | 0.344 | 1 | 17.3 | 84.2 | 88.1 |
| 17 | 0.354 | 1 | 28.4 | 79.8 | 85.3 |
| 34 | 0.372 | 1 | 22.9 | 80 | 85.4 |
| 36 | 0.380 | 1 | 17 | 87.4 | 81.2 |
| 31 | 0.384 | 1 | 22.8 | 80.8 | 87.3 |
| 22 | 0.384 | 1 | | 81.6 | 82 |
| 18 | 0.386 | 1 | 22.2 | 84.3 | 83.5 |
| 26 | 0.402 | 1 | 15.3 | 84.2 | 82.2 |
| 11 | 0.406 | 1 | 17.8 | 83.4 | 87.6 |
| 21 | 0.444 | 1 | 9 | 82.7 | 83.9 |
| 5 | 0.498 | 1 | 9 | 85.3 | 85.9 |
| 13 | 0.522 | 1 | 15.8 | 91.1 | 80.0 |
| 12 | 0.602 | 1 | 12.8 | 88.6 | 79.8 |
| 19 | 0.652 | 1 | 15 | 93.1 | 84.4 |
| 15 | 0.670 | 1 | 11.3 | 90.2 | 80.5 |
| 20 | 0.682 | 1 | 9.8 | 95 | 91.9 |
| 10 | 0.696 | 1 | 12.8 | 93.4 | 78.6 |
| 24 | 0.486 | 1.714 | | 92.8 | 75.4 |
| 33 | 0.582 | 1.714 | 7.82 | 95.3 | 64.5 |
| 35 | 0.510 | 1.862 | 9.56 | 84.9 | 72.0 | show that at a CRS:methyl iodide ratio of 1:1, as the amount of total water fed to the mixer (excluding water already added to the process stream to hydrolyses the acetic anhydride) was increased from about 0.26 of the mass of the process stream (CRS) to about 0.70 of the mass of the process stream (CRS), the rhodium extraction efficiency in the pre-extraction aqueous phase decreased from about 25% to about 10% whereas the tar extraction efficiency into the pre-extraction methyl iodide phase increased from about 70% to about 95% and the catalyst stabiliser efficiency changed from 87% to 82%. Changing the ratio of methyl iodide to process stream gave no significant change in the rhodium extraction efficiency and in the tar extraction efficiency when changes in the water rate were taken into account in these experiments. The distribution efficiency of quaternary amine iodide salt (QAS) was reduced by about 10% by increasing the ratio of methyl iodide to process stream in these experiments. Overall the extraction efficiency of the iodide salt was about 85% across all the experiments performed.

Product from the pre-extraction step experiment was used in further experiments to demonstrate the extraction/separation using extracting solution comprising iodide salt co-promoter according to step (b) of the present invention. A glass Kuhni column was used which had an internal diameter of 18 mm, a working length of 1.2 m and an effective volume of about 240 ml. A 12 mm PTFE paddle was provided down the centre of the column with feeds being pumped in by positive displacement pumps. The phase interphase was maintained by a weir at the base of the column. The column was maintained at a controlled temperature of ±0.1° C. using a circulating water jacket.

The acetic acid content of the pre-extraction aqueous phase was analysed and adjusted to a pre-determined value by the addition of glacial acetic acid. Methyl iodide was also added to saturate the solution; any excess being decanted off. In these experiments the concentration of components after adjustment in the extracting solution fed to the Kuhni column were: QAS from about 3 to 11% by weight; methyl iodide from about 19 to 34% by weight; acetic acid from about 40 to 56% by weight; water from about 13 to 20% by weight; methyl acetate for about 0.7 to 4.5%; tar from about 0.5 to 3.5% by weight and rhodium about 15 to 150 ppm.

The feed rates of the pre-extraction phases to the Kuhni column were adjusted to correspond to the product rates from the pre-extraction step had the two steps been integrated and operated together.

The effect of different acetic acid/water ratios in the extracting solution on the rhodium and tar extraction efficiencies in the Kuhni column at 20° C. are shown in Table 2 for two different ratios of CRS/water used in the pre-extraction stage. It will be seen that the lower the amount of water used in the pre-extraction, the lower the ratio of acid: water required to achieve a given rhodium efficiency, presumably this is due to the higher concentration of iodide salt in the extracting solution. Tar efficiency shows the opposite trend.

Table 3 shows the effect of acid: water ratio at two different ratios of CRS:methyl iodide in the pre-extraction. At a CRS:methyl iodide ratio of 0.6:1 the efficiences were very sensitive to acid:water ratios. The results also show a reduction in QAS efficiency at high tar efficiencies as QAS in removed with the tar in the base methyl iodide phase from the Kuhni column.

Comparison experiments (numbers 1 and 37) were performed without the iodide salt and pre-extraction using methyl iodide-saturated aqueous acetic acid solutions having compositions of acetic acid: water: methyl iodide of approximately 60:15:25. (Experiment 1 acid:-water ratio=3.3:1; Experiment 37 acid:water ratio=3.8:1). The weight ratio of composition comprising methyl iodide and tar:extraction solution was 0.28:1 for Experiment 1 and 0.21:1 for Experiment 37. The stream compositions are shown in Table 4. The rhodium extraction efficiencies were 74% and 87% and tar extraction efficiencies were 31 and 14% for Experiments 1 and 37 respectively. Using the data in Table 2, the acid/water ratios necessary to achieve the rhodium efficiencies of the comparison experiments were determined by extropolation and these were then used to estimate the expected tar efficiencies in the process according to the present invention for rhodium efficiencies of 74% and 87%. For a CRS:water ratio of 2.6:1 the tar efficiencies would be expected to be 50% and 41% respectively and for a CRS:water value of 1.5:1 the tar efficiencies would be expected to be 38% and 22%. These are significantly better than those achieved without the iodide salt and pre-extraction.

Thus the process of the present invention allows for increased tar extraction efficiency at rhodium extraction efficiencies of known processes or, since tar and rhodium extraction efficiencies are inversely related, an increased rhodium extraction may be obtained for tar extraction efficiencies corresponding to known processes.

Figure 2:
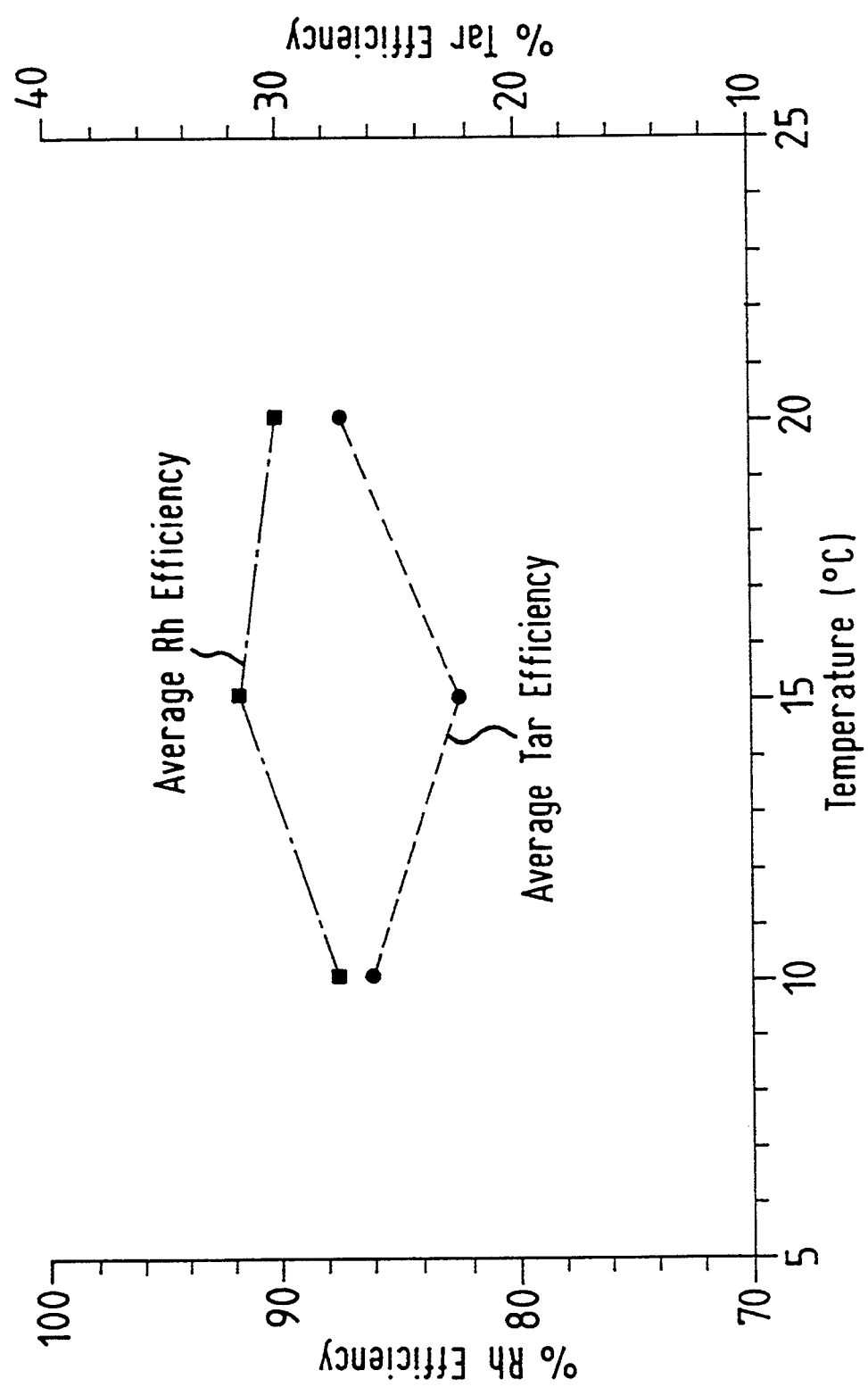

FIG. 2 shows average rhodium and tar extraction efficiencies in the Kuhni column at different temperatures and at a CRS:water ratio of 2.6:1 in the pre-extraction, an acetic acid:water ratio of 3.0:1 in the extracting solution feed and a CRS:methyl iodide ratio of 1:1.

TABLE 2

EFFECT OF ACID/WATER RATIO AT TWO PRE-EXTRACTION FEED RATES

| Expt. No. | CRS Water Ratio | Acid/Water Feed Ratio | Rh Eff. % | Tar Eff. % | QAS Eff. % |
|---|---|---|---|---|---|
| 19 | 1.53 | 4.0 | 98 | 14 | 99.7 |
| 15 | 1.49 | 3.6 | 95 | 24 | 98.6 |
| 20 | 1.47 | 3.5 | 91 | 20 | 99.2 |
| 18 | 2.59 | 3.0 | 98 | 26 | 98.7 |
| 17 | 2.82 | 2.85 | 95 | 16 | 98.4 |
| 11 | 2.46 | 2.7 | 89 | 32 | 98.3 |
| 26 | 2.49 | 2.6 | 85 | 35 | 97.8 |

Note:
CRS/MeI = 1

TABLE 3

EFFECT OF ACID/WATER RATIO AT TWO DIFFERENT CRS/MeI RATIOS

| Expt. No. | CRS Water Ratio | CRS MeI Ratio | Acid/Water Feed Ratio | Rh Eff. % | Tar Eff. % | QAS Eff. % |
|---|---|---|---|---|---|---|
| 29 | 2.96 | 1.37 | 2.4 | 80 | 23 | 98.6 |
| 30 | 2.92 | 1.37 | 3.0 | 97 | 9 | 99.4 |
| 23 | 2.94 | 1.37 | 3.2 | 97 | 6 | 99.5 |
| 33 | 1.72 | 0.58 | 2.5 | 26 | 56 | 94.8 |
| 35 | 1.96 | 0.54 | 2.8 | 26 | 58 | 95.7 |
| 24 | 2.06 | 0.58 | 3.0 | 68 | 41 | 97.0 |

TABLE 4

COMPOSITIONS FOR COMPARISON EXPERIMENTS

| | Experiment 1 | Experiment 37 |
|---|---|---|
| Composition of Methyl Iodide - Diluted Tar | | |
| Rhodium (ppm) | 365 | 340 |
| Tar (% by weight) | 11 | 9.4 |
| QAS (% by weight) | 9 | 9 |
| Water (% by weight) | 4.7 | 5.1 |
| Methyl iodide (% by weight) | 42.8 | 47.3 |
| Methyl acetate (% by weight) | 5.7 | 6.0 |
| Acetic acid (% by weight) | 19.5 | 19.3 |
| Composition of Extracting Solution | | |
| Water (% by weight) | 17.7 | 14.8 |
| Methyl iodide (% by weight) | 23.1 | 27.7 |
| Methyl acetate (% by weight) | 0.9 | 0.3 |
| Acetic acid (% by weight) | 58.8 | 56.3 |

I claim:

1. A process for the recovery of Group VIII noble metal catalyst from a process stream comprising Group VIII noble metal carbonylation catalyst and tar, said tar having been generated during a carbonylation process for the production of carboxylic acid anhydride in the presence of a Group VIII noble metal carbonylation catalyst, a halide promoter and an iodide salt co-promoter, said recovery process comprising the steps of:
   (a) mixing said process stream with alkyl halide to produce a composition comprising alkyl halide, tar and Group VIII noble metal catalyst;
   (b) contacting the composition from step (a) with an extracting solution comprising (i) water, (ii) carboxylic acid corresponding to said carboxylic acid anhydride product of said carbonylation process, (iii) iodide salt co-promoter derived from said carbonylation process and (iv) alkyl halide, to produce an aqueous phase comprising Group VIII noble metal catalyst and an alkyl halide phase comprising tar; and
   (c) separating said aqueous and alkyl halide phases.

2. A process as claimed in claim 1 in which the iodide salt co-promoter in said extracting solution is derived from said carbonylation process in a pre-extraction step in which step a process stream comprising iodide salt co-promoter, Group VIII noble metal carbonylation catalyst, carboxylic acid anhydride or the corresponding carboxylic acid thereof and tar, is mixed with alkyl halide and water to produce (i) a pre-extraction aqueous phase comprising water, carboxylic acid corresponding to the carboxylic acid anhydride product of said carbonylation process, alkyl halide and iodide salt co-promoter, and (ii) a pre-extraction alkyl halide phase comprising alkyl halide, tar and Group VIII noble metal catalyst; and in which said pre-extraction phases are separated and said pre-extraction aqueous phase is used for at least part of said extracting solution in step (b).

3. A process as claimed in claim 2 in which said process stream comprising iodide salt co-promoter, Group VIII noble metal carbonylation catalyst, carboxylic acid anhydride or the corresponding carboxylic acid thereof and tar is obtained from said carbonylation process by withdrawing a liquid carbonylation composition comprising a Group VIII noble metal carbonylation catalyst, a halide promoter, an iodide salt co-promoter, carboxylic acid anhydride or the corresponding carboxylic acid thereof, carbonylation reactant and tar and subjecting said liquid carbonylation composition to a flash separation with or without the addition of heat to produce (a) a vapour fraction and (b) a liquid fraction comprising Group VIII noble metal carbonylation catalyst, iodide salt co-promoter, carboxylic acid anhydride or the corresponding carboxylic acid thereof and tar.

4. A process as claimed in claim 2 in which the concentrations of water, carboxylic acid or alkyl halide in said pre-extraction aqueous phase are adjusted by addition of water, carboxylic acid or alkyl halide before use for at least part of the extracting solution in step (b).

5. A process as claimed in claim 2 in which said pre-extraction aqueous phase comprises 60 to 90% of said iodide salt co-promoter from said process stream comprising iodide salt, Group VIII noble metal, carboxylic acid anhydride or its corresponding acid and tar.

6. A process as claimed in claim 1 in which the carboxylic acid anhydride product of said carbonylation process comprises acetic anhydride.

7. A process as claimed in claim 6 in which said Group VIII noble metal comprises rhodium.

8. A process as claimed in claim 7 in which said carbonylation halide promoter and said alkyl halide comprise methyl iodide.

9. A process as claimed in claim 8 in which said iodide salt co-promoter comprises an iodide salt selected from the group consisting of iodide salts of quaternary amine, phosphine, arsine and stibine; chromium; zircontum; vanadium and lithium.

10. A process as claimed in claim 9 in which said iodide salt co-promoter comprises N,N' dimethyl imidazolium iodide or an alkylated derivative thereof.

11. A process as claimed in claim 9 in which said iodide salt co-promoter comprises lithium iodide.

* * * * *

UNITED STATES PATENT AND TRADEMARK OFFICE
CERTIFICATE OF CORRECTION

PATENT NO. : 5,364,822
DATED : November 15, 1994
INVENTOR(S) : JOHN J. CAREY

It is certified that error appears in the above-indentified patent and that said Letters Patent is hereby corrected as shown below:

Col. 8, lines 12-23, rewrite these lines to read as follows:

--rhodium efficiency (%) =

$$\frac{\text{mass flow rate of rhodium in aqueous phase} \times 100}{\text{mass flow rate of rhodium in aqueous and alkyl halide phases}}$$

tar efficiency (%) =

$$\frac{\text{mass flow rate of tar in alkyl halide} \times 100}{\text{mass flow rate of tar in alkyl halide and aqueous phases}}$$

quaternary amine $_{salt}$ (QAS) efficiency (%) =

$$\frac{\text{mass flow rate of quaternary amine salt in aqueous phase} \times 100}{\text{mass flow rate of QAS in aqueous and alkyl halide phases}}.--$$

Col. 12, l. 57, correct the spelling of the word "zirconium"

Signed and Sealed this

Twenty-fifth Day of April, 1995

*Attest:*

BRUCE LEHMAN

*Attesting Officer*     *Commissioner of Patents and Trademarks*